United States Patent
Maeda et al.

[11] Patent Number: 6,030,990
[45] Date of Patent: Feb. 29, 2000

[54] N-BENZYLDIOXOTHIAZOLIDYLBENZAMIDE DERIVATIVES AND PROCESS FOR PRODUCING THE SAME

[75] Inventors: Toshio Maeda; Masahiro Nomura, both of Nogi-machi; Katsuya Awano, Oyama; Susumu Kinoshita, Shiraoka-machi; Hiroya Satoh, Nogi-machi; Koji Murakami, Nogi-machi; Masaki Tsunoda, Nogi-machi, all of Japan

[73] Assignee: Kyorin Pharmaceutical Co., Ltd., Tokyo, Japan

[21] Appl. No.: 08/952,672

[22] PCT Filed: May 30, 1996

[86] PCT No.: PCT/JP96/01459

§ 371 Date: Dec. 2, 1997

§ 102(e) Date: Dec. 2, 1997

[87] PCT Pub. No.: WO96/38428

PCT Pub. Date: Dec. 5, 1996

[30] Foreign Application Priority Data

Jun. 2, 1995 [JP] Japan ..................... 7-159781
May 24, 1996 [JP] Japan ..................... 8-153139

[51] Int. Cl.[7] ..................... A61K 31/425; C07D 277/34
[52] U.S. Cl. ..................... 514/369; 548/183
[58] Field of Search ..................... 548/183; 514/369

[56] References Cited

FOREIGN PATENT DOCUMENTS 1-272573  10/1989  Japan .
5-2555288  10/1993  Japan .
5-213913  4/1995  Japan .

Primary Examiner—Laura L. Stockton
Attorney, Agent, or Firm—Oblon, Spivak, McClelland, Maier & Neustadt, P.C.

[57] ABSTRACT

The present invention provides novel N-benzyldioxothiazolidylbenzamide derivatives that improve the insulin resistance and have potent hypoglycemic and lipid-lowering effects and processes for preparing the same, and relates to N-benzyldioxothiazolidylbenzamide derivatives characterized by being represented by a general formula (1)

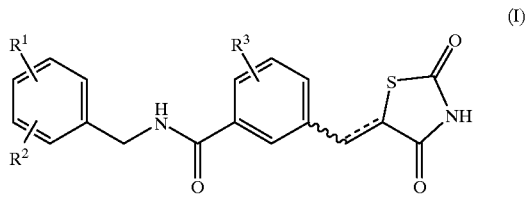

wherein $R^1$ and $R^2$ denote identically or differently hydrogen atoms, lower alkyl groups with carbon atoms of 1 to 4, lower alkoxy groups with carbon atoms of 1 to 3, lower haloalkyl groups with carbon atoms of 1 to 3, lower haloalkoxy groups with carbon atoms of 1 to 3, halogen atoms, hydroxyl groups, nitro groups, amino groups which may be substituted with lower alkyl group(s) with carbon atoms of 1 to 3 or hetero rings, or $R^1$ and $R^2$ link to form a methylenedioxy group, $R^3$ denotes a lower alkoxy group with carbon atoms of 1 to 3, hydroxyl group or halogen atom, and dotted line indicates double bond or single bond in combination with solid line, and processes for preparing the same.

13 Claims, No Drawings

N-BENZYLDIOXOTHIAZOLIDYLBENZAMIDE DERIVATIVES AND PROCESS FOR PRODUCING THE SAME

This application is a 371 of PCT/JP96/01459 filed May 30, 1996.

TECHNICAL FIELD

The present invention relates to novel N-benzyldioxothiazolidylbenzamide derivatives that improve the diabetes mellitus and the hyperlipidemia, and processes for preparing the same.

BACKGROUND TECHNOLIGIES

So far, as oral therapeutic drugs for diabetes mellitus, biguanide type and sulfonylurea type compounds have been used. However, with biguanide type compounds, lactic acidosis or hypoglycemia is caused and, with sulfonylurea type compounds, serious and prolonged hypoglycemia is caused, and the adverse effect thereof is posing a problem, hence the appearance of new therapeutic drug for diabetes mellitus without such defects is desired. It is also known that some of thiazolidine-2,4-dione derivatives exhibit hypoglycemic and lipid-lowering effects (Journal of Medicinal Chemistry, Vol. 35, P. 1853 (1992), Published Unexamined Patent Application No. Hei 1-272573), but, in all of these compounds, the substituted position of middle benzene ring that connects thiazolidine-2,4-dione ring and aromatic ring is p-position, or the middle benzene ring has no substituent, further the aromatic ring of the former is oxazol ring, the linkage of the latter is through sulfonamide, and the like, which differ structurally from compounds of the invention, N-benzyldioxothiazolidylbenzamide derivatives.

For the non-insulin dependent diabetes mellitus (NIDDM) accounting for the majority of diabetics, a blood sugar-lowering drug that improves the insulin resistance and has high safety and effectiveness is strongly desired.

As a result of diligent studies on a drug that improves the insulin resistance and has potent hypoglycemic effects and high safety, the inventors have found that novel N-benzyldioxothiazolidylbenzamide derivatives represented by a following general formula (1) have excellent hypoglycemic and lipid-lowering effects, leading to the completion of the invention.

DISCLOSURE OF THE INVENTION

Namely, the invention provides N-benzyldioxothiazolidylbenzamide derivatives represented by a general formula (1)

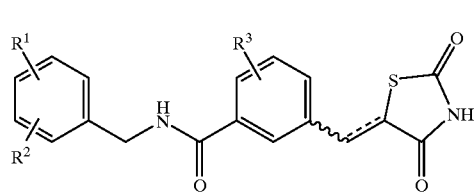

(I)

[wherein $R^1$ and $R^2$ denote identically or differently hydrogen atoms, lower alkyl groups with carbon atoms of 1 to 4, lower alkoxy groups with carbon atoms of 1 to 3, lower haloalkyl groups with carbon atoms of 1 to 3, lower haloalkoxy groups with carbon atoms of 1 to 3, halogen atoms, hydroxyl groups, nitro groups, amino groups which may be substituted with lower alkyl group(s) with carbon atoms of 1 to 3 or hetero rings, or $R^1$ and $R^2$ link to form a methylenedioxy group, $R^3$ denotes a lower alkoxy group with carbon atoms of 1 to 3, hydroxyl group or halogen atom, and dotted line indicates double bond or single bond in combination with solid line], and their pharmacologically acceptable salts.

The salts of compounds represented by the general formula (1) in the invention are of common use, and pharmacologically acceptable metal salts such as alkali metal salts (e.g. sodium salt, potassium salt, etc.), alkaline earth metal salts (e.g. calcium salt, magnesium salt, etc.) and aluminum salt can be mentioned.

Moreover, the general formula (1) in the invention sometimes includes stereoisomers based on double bond and optical isomers based on thiazolidine portion. Such isomers and their mixtures are all to be included in the scope of this invention.

In the general formula (1) of the invention, for "lower alkyl group", straight or branched chain groups with carbon atoms of 1 to 4 such as methyl, ethyl, propyl and butyl are mentioned.

For "lower alkoxy group", straight or branched chain groups with carbon atoms of 1 to 3 such as methoxy, ethoxy and propoxy are mentioned.

For "lower haloalkyl group", straight or branched chain groups with carbon atoms of 1 to 3 such as trifluoromethyl are mentioned.

For "lower haloalkoxy group", straight or branched chain groups with carbon atoms of 1 to 3 such as trifluoromethoxy are mentioned.

For "halogen atom", fluorine atom, chlorine atom, bromine atom and iodine atom are mentioned.

For "amino group which may be substituted with lower alkyl group", amino group, or methylamino group, ethylamino group, dimethylamino group, diethylamino group, etc., in which one or two hydrogen atoms are substituted with straight or branched chain lower alkyl group with carbon atoms of 1 to 3 such as methyl, ethyl and propyl, are mentioned.

According to the invention, compounds of said general formula (1) can be prepared through following processes.

Compounds of general formula (1) can be prepared by reacting compounds of general formula (7) with compounds of general formula (11).

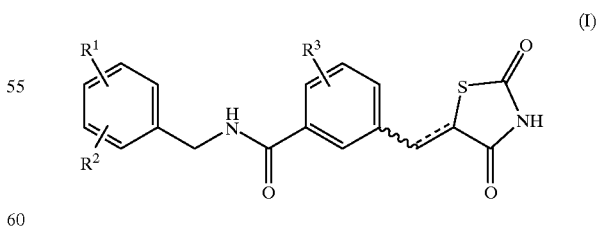

(I)

[wherein $R^1$ and $R^2$ denote identically or differently hydrogen atoms, lower alkyl groups with carbon atoms of 1 to 4, lower alkoxy groups with carbon atoms of 1 to 3, lower haloalkyl groups with carbon atoms of 1 to 3, lower haloalkoxy groups with carbon atoms of 1 to 3, halogen atoms, hydroxyl groups, nitro groups, amino groups which may be substituted with lower alkyl group(s) with carbon atoms of 1 to 3 or hetero rings, or $R^1$ and $R^2$ link to form a methylenedioxy group, $R^3$ denotes a lower alkoxy group with carbon atoms of 1 to 3, hydroxyl group or halogen atom, and dotted line indicates double bond or single bond in combination with solid line]

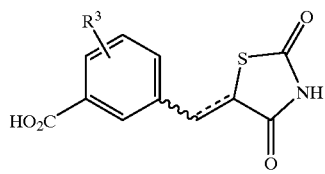

(7)

[wherein $R^3$ and dotted line are as described above]

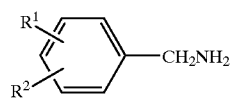

(II)

[wherein $R^1$ and $R^2$ are as described above]

The reaction can be conducted by treating with condensing agent, for example, 1-ethyl-3-(3'-dimethylaminopropyl) carbodiimide, diethyl cyanophosphate or the like in an organic solvent, for example, dimethyl sulfoxide, N,N-dimethylformamide or the like. Moreover, if need be, an organic base, for example, triethylamine or the like may be added.

As the reaction temperature, ice cooling to room temperature can be used.

Compounds of general formula (1b) can be prepared by reducing compounds of general formula (1a).

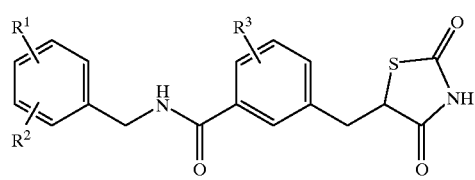

(Ib)

[wherein $R^1$, $R^2$ and $R^3$ are as described above]

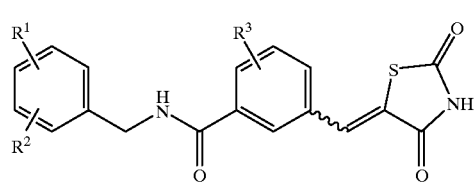

(Ia)

[wherein $R^1$, $R^2$ and $R^3$ are descried above]

The reaction can be conducted by hydrogenating at ambient pressure to 4 kg/cm² in the presence of catalyst such as palladium/carbon in an organic solvent, for example, ethanol, ethyl acetate, N,N-dimethylformamide or the like or in a mixed solvent thereof at room temperature to heating. Or, it can be conducted by treating with sodium amalgam in an organic solvent, for example, alcohol such as ethanol or in a mixed solvent with water at room temperature to heating.

Compounds of following general formula (1d) can be prepared by reacting general formula (1c) with Lewis acid.

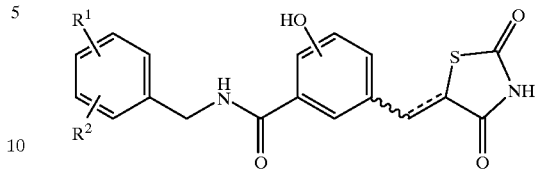

(Id)

[wherein $R^1$, $R^2$ and dotted line are as described above]

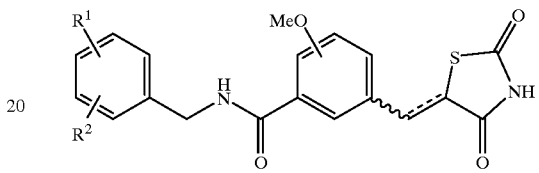

(Ic)

[wherein $R^1$, $R^2$ and dotted line are as described above]

The reaction can be conducted by treating with Lewis acid, for example, boron tribromide, boron trichloride or the like in an organic solvent, for example, dichloromethane, chloroform or the like at −78° C. to room temperature.

Compounds of general formula (7) can be prepared by hydrolyzing compounds of following general formula (6)

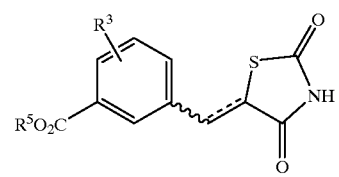

(6)

[wherein $R^3$ and dotted line are as described above, and $R^5$ denotes a lower alkyl group with carbon atoms of 1 to 3]

The reaction can be conducted under acidic or alkaline condition employing cooling to solvent refluxing as reaction temperature and, for example, refluxing under heat in a mixed solvent of acetic acid with concentrated hydrochloric acid is preferable.

Compounds of general formula (4) can be prepared by reacting compounds of following general formula (2) with compound of formula (3).

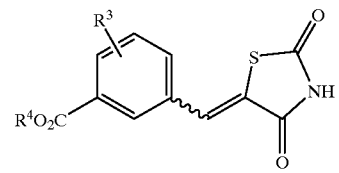

(4)

[wherein $R^3$ is as described above, and $R^4$ denotes a hydrogen atom or lower alkyl group with carbon atoms of 1 to 3]

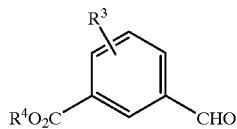

(2)

[wherein $R^3$ and $R^4$ are as described above]

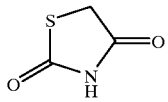

(3)

The reaction can be conducted in an organic solvent, for example, benzene, toluene, xylene or the like at room temperature to solvent-refluxing temperature as reaction temperature, but the solvent-refluxing temperature is preferable. Moreover, as a catalyst, addition of secondary amine (piperdine or the like) or acetic acid salt (ammonium acetate or the like) and acetic acid is suitable.

Also, it can be conducted by heating together with base (sodium acetate, piperidine or the like) without solvent.

Compounds of general formula (5) can be prepared by reducing compounds general formula (4).

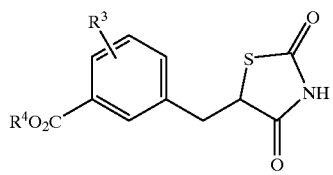

(5)

[wherein $R^3$ and $R^4$ are as described above]

The reaction can be conducted by hydrogenating at ambient pressure to 4 kg/cm² in the presence of catalyst such as pallidium/carbon in an organic solvent, for example, ethanol, ethyl acetate, N,N-dimethylformamide or the like or in a mixed solvent thereof at room temperature to heating.

Or, it can be conducted by treating with sodium amalgam in an organic solvent, for example, alcohol such as ethanol or in a mixed solvent with water at room temperature to heating.

Compounds of general formula (7a) can be prepared by reacting compounds of following general formula (10) with thiourea, followed by hydrolysis.

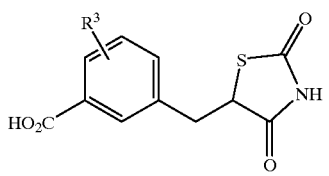

(7a)

[wherein $R^3$ is as described above]

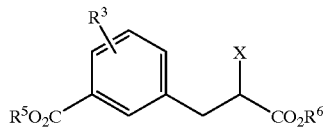

(10)

[wherein $R^3$ and $R^5$ are as described above, $R^6$ denotes a lower alkyl group with carbon atoms of 1 to 3, and X denotes a halogen atom]

The reaction between compounds of general formula (10) and thiourea can be conducted in an organic solvent, for example, alcohol such as ethanol at room temperature to solvent refluxing temperature, but the solvent refluxing temperature is preferable. If need be, a base (sodium acetate or the like) may be added. Successive hydrolysis reaction can be conducted under acidic condition and, for example, it is preferable to reflux under heat in hydrochloric acid or in a mixed solvent of hydrochloric acid with organic solvent (sulforane or the like).

Compounds of general formula (10) can be prepared by converting compounds of general formula (8) to diazonium salts and then conducting Meerwein arylation with Compounds of general formula (9).

(8)

R⁵O₂C—[ring with R³]—NH₂

[wherein $R^3$ and $R^5$ are as described above]

(9)

CH₂=CH—CO₂R⁶

[wherein $R^6$ is as described above]

The reaction can be conducted by diazotizing compounds of general formula (8) with nitrite such as sodium nitrite in an organic solvent, for example, alcohol such as methanol or ethanol, ketone such as acetone or methyl ethyl ketone or water or in a mixed solvent thereof in the presence of hydrogen halide such as hydrochloric acid or hydrobromic acid, and then reacting with catalytic amount of cuprous salt such as cuprous oxide or cuprous chloride in the presence of compounds of general formula (9)

In following, the invention will be illustrated based on concrete examples, but the invention is not confined to these examples. The abbreviated terms used in examples represent following meanings.

| | |
|---|---|
| $^1\text{H}$ NMR | Proton nuclear magnetic resonance spectrum |
| MS | Mass spectrum |
| CDCl₃ | Deuterated chloroform |
| DMF | N,N-dimethylformamide |
| DMSO | Dimethyl sulfoxide |
| THF | Tetrahydrofuran |
| d₆-DMSO | Deuterated dimethyl sulfoxide |

EXAMPLE 1

Methyl 5-(2,4-dioxothiazolidin-5-ylidene)methyl-2-methoxybenzoate

A mixture of methyl 5-formyl-2-methoxybenzoate (490 mg), thiazolidine-2,4-dione (358 mg), ammonium acetate (401 mg), acetic acid (0.8 ml) and benzene (10 ml) was submitted to Dean-Stalk dewatering apparatus to reflux for 4 hours under heat. After cooling, the crystals deposited were collected by filtration, washed with benzene and with 20% aqueous solution of acetone, and then dried to obtain 634 mg (86%) of aimed compound as crystals.

$^1$H NMR (d$_6$-DMSO), δ:3.83(3H, s), 3.90(3H, s), 7.34 (IH, d, J=9.3 Hz), 7.79(1H, s), 7.76–7.83(1H, m), 7.87–7.92 (1H, m), 12.59(1H, s)

EXAMPLES 2 AND 3

Similarly to Example 1, compounds in Table 1 were obtained.

TABLE 1

| Example | R$^3$ | R$^4$ | Property | MS(m/z):M$^+$ |
|---|---|---|---|---|
| 2 | EtO | Et | Crystal | — |
| 3 | i-PrO | H | Crystal | 307 |

EXAMPLE 4

Methyl 5-(2,4-dioxothiazolidin-5-yl)methyl-2-methoxybenzoate

Methyl 5-(2,4-dioxothiazolidin-5-ylidene)methyl-2-methoxy-benzoate (9.52 g) was suspended into DMF (250 ml) and hydrogenated with 10% palladium/carbon (10.0 g) at room temperature under a hydrogen pressure of 3.5 kg/cm$^2$. After the reaction, the solution was filtered and concentrated and water was added to the residue, which was extracted with ethyl acetate. The organic layer was washed with saturated brine, dried over anhydrous sodium sulfate and concentrated under reduced pressure. The residue was purified by means of silica gel column chromatography (developing solvent; methylene chloride:acetone=50:1) to obtain 5.88 g (61%) of aimed compound as an amorphous material.

MS(m/z):295(M$^+$)

EXAMPLE 5

5-(2,4-Dioxothiazolidin-5-ylidene)methyl-2-methoxybenzoic acid

A suspension of methyl 5-(2,4-dioxothiazolidin-5-ylidene)-methyl-2-methoxybenzoate (629 mg) in acetic acid-concentrated hydrochloric acid (1:1, 18.0 ml) was refluxed for 6 hours under heat. After cooling, water (36 ml) was added and the crystals were collected by filtration, washed with water and dried to obtain 599 mg (100%) of aimed compound as crystals.

$^1$H NMR (d$_6$-DMSO), δ:3.89(3H, s), 7.31(1H, d, J=8.8 Hz), 7.76(1H, dd, J=2.4, 8.81 Hz), 7.79(1H, s), 7.89(1H, d, J=2.41 Hz), 12.58(1H, s), 12.91(1H, br)

EXAMPLE 6 AND 7

Similarly to Example 5, compounds in Table 2 were obtained.

TABLE 2

| Example | R$^3$ | Dotted line portion | Property | MS(m/z):M$^+$ |
|---|---|---|---|---|
| 6 | MeO | Single bond | Crystal | — |
| 7 | Eto | Double bond | Crystal | 293 |

EXAMPLE 8

Methyl 2-bromo-3-(3-methoxycarbonyl-4-fluorophenyl)propiona te

To a solution of methyl 5-amino-2-fluorobenzoate (4.12 g) in 47% hydrobromic acid (11.4 ml), methanol (20 ml) and acetone (50 ml), a solution of sodium nitrite (1.88 g) in water (3 ml) was slowly added dropwise under cooling with salt-ice and stirring so as to keep an internal temperature of not higher than −5° C. After stirred for 30 minutes as it was, ice bath was removed, methyl acrylate (13.3 ml) was added, and cuprous oxide (225 mg) was added little by little while stirring vigorously. After no nitrogen became to generate, the reaction liquor was concentrated under reduced pressure. The residue was dissolved into ethyl acetate, washed with water, saturated aqueous solution of sodium hydrogencarbonate and water in order, dried over anhydrous sodium sulfate, and concentrated under reduced pressure. The residue was purified by means of silica gel column chromatography (developing solvent; n-hexane:ethyl acetate=10:1) to obtain 3.48 g (45%) of aimed compound as an oily material.

$^1$H NMR (CDCl$_3$), δ:3.25(1H, dd, J=7.3, 14.6 Hz), 3.46 (1H, dd, J=7.8, 14.2 Hz), 3.75(3H, s), 3.93(3H, s), 4.38(1H, t, J=7.8 Hz), 7.09(1H, dd, J=8.8, 10.8 Hz), 7.38(1H, ddd, J=2.4, 4.4, 8.8 Hz), 7.80(1H, dd, J 2.4, 6.3 Hz); MS(m/z) :318, 320(M$^+$)

EXAMPLES 9 AND 10

Similarly to Example 8, compounds in Table 3 were obtained.

TABLE 3

| Example | R$^3$ | R$^5$ | R$^6$ | Property | MS(m/z):M$^+$ |
|---|---|---|---|---|---|
| 9 | 6-MeO | Et | Me | Oily material | 344 |
| 10 | 2-MeO | Me | Me | Oily material | 330, 332 |

EXAMPLE 11

5-(2,4-Dioxothiazolidin-5-yl)methyl-2-fluorobenzoic acid

To a solution of methyl 2-bromo-3-(3-methoxycarbonyl-4-fluorophenyl)propionate (1.22 g) in ethanol (40 ml), thiourea (356 mg) was added and the mixture was refluxed for 11 hours under heat. After cooling, this was concentrated under reduced pressure and water (50 ml) was added to the residue. After pH was adjusted to around 8 with saturated aqueous solution of sodium bicarbonate under stirring, ether (20 ml) and n-hexane (40 ml) were added, which was stirred for 10 minutes as it was. The crystals were collected by filtration, washed with water, and then dried. The solids thus obtained were dissolved into sulforane (10 ml) and, after 6N hydrochloric acid (20 ml) was added, the mixture was refluxed for 8 hours under heat. After cooling, this was poured into ice water and the crystals deposited were collected by filtration, washed with water, and then dried to obtain 403 mg (39%) of aimed compound as crystals.

$^1$H NMR (d$_6$-DMSO), δ:3.22(1H, dd, J=8.3, 14.2 Hz), 3.51(1H, dd, J=4.4, 14.2 Hz), 4.95(1H, dd, J=4.4, 8.3 Hz), 7.27(1H, dd, J=8.3, 10.8 Hz), 7.51(1H, ddd, J=2.5, 4.9, 8.3 Hz), 7.74(1H, dd, J=2.5, 6.8 Hz), 12.05(1H, s), 13.28(1H, s); MS(m/z):269(M$^+$)

EXAMPLES 12 AND 13

Similarly to Example 11, compounds in Table 4 were obtained.

TABLE 4

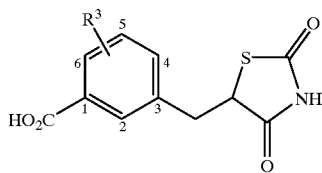

| Example | R$^3$ | Property | MS(m/z):M$^+$ |
|---|---|---|---|
| 12 | 4-MeO | Crystal | 281 |
| 13 | 2-Meo | Crystal | 281 |

EXAMPLE 14

N-(4-Trifluoromethylbenzyl)-5-(2,4-dioxothiazolidin-5-ylidene)methyl-2-methoxybenzamide To a solution of 5-(2,4-dioxothiazolidin-5-ylidene)methyl-2-methoxybenzoic acid (1.00 g) and 4-trifluoromethylbenzylamine (627 mg) in DMF (10 ml), diethyl cyanophosphate (615 mg) and triethylamine (370 mg) were added at room temperature in an argon atmosphere under stirring, and the mixture was stirred for 5 hours as it was. The reaction liquor was poured into ice water and the crystals deposited were collected by filtration, washed with water, and then dried to obtain 1.31 g (84%) of aimed compound as crystals. Further, these were recrystallized from ethanol to obtain purified aimed compound as yellow prismatic crystals. Melting point 210.0~211.5° C.

Elemental analysis (%): For C$_{20}$H$_{15}$F$_3$N$_2$O$_4$S

|  | C | H | N |
|---|---|---|---|
| Calculated | 55.04 | 3.46 | 6.42 |
| Found | 55.30 | 3.36 | 6.48 |

EXAMPLES 15 THROUGH 38

Similarly to Example 14, compounds in Table 5 and Table 6 were obtained.

TABLE 5

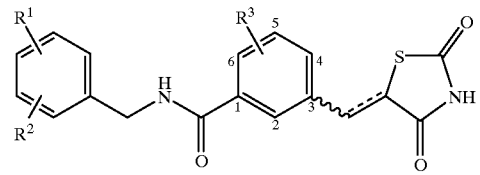

| Ex-ample | R$^1$ · R$^2$ | R$^3$ | Dotted line portion | Melting point (°C.) (Recrystallization solvent) | Composition formula | Elemental analysis (%) Calculated/Found |  |  |
|---|---|---|---|---|---|---|---|---|
|  |  |  |  |  |  | C | H | N |
| 15 | H | 6-MeO | Single bond | Amorphous | C$_{19}$H$_{18}$N$_2$O$_4$S | 61.61<br>61.94 | 4.90<br>5.10 | 7.56<br>7.35 |
| 16 | H | 6-MeO | Double bond | 209.0~212.0 (Suspended into hexane) | C$_{19}$H$_{16}$N$_2$O$_4$S | 61.94<br>62.32 | 4.38<br>4.50 | 7.61<br>7.48 |
| 17 | 3-CF$_3$ | 6-MeO | Single bond | 145.0~147.0 (Ethyl acetate-hexane) | C$_{20}$H$_{17}$F$_3$N$_2$O$_4$S | 54.79<br>54.68 | 3.91<br>3.85 | 6.39<br>6.27 |
| 18 | 3-CF$_3$ | 6-MeO | Double bond | 188.0~190.0 (Ethanol) | C$_{20}$H$_{15}$F$_3$N$_2$O$_4$S · H$_2$O | 52.86<br>52.78 | 3.77<br>3.72 | 6.17<br>6.18 |

TABLE 5-continued

[Structure: R¹, R² on benzyl ring attached to NH-C(=O)- on benzene ring (positions 1,2,3 labeled, with R³ at 5,6 position), connected via methylene (position 4) to 2,4-dioxothiazolidin-5-ylidene]

| Example | R¹·R² | R³ | Dotted line portion | Melting point (°C.) (Recrystallization solvent) | Composition formula | Elemental analysis (%) Calculated/Found C | H | N |
|---|---|---|---|---|---|---|---|---|
| 19 | 2-$CF_3$ | 6-MeO | Single bond | 179.0~181.0 (Ethyl acetate-hexane) | $C_{20}H_{17}F_3N_2O_4S$ | 54.79 / 54.58 | 3.91 / 3.98 | 6.39 / 6.30 |
| 20 | 2-$CF_3$ | 6-MeO | Double bond | 197.0~199.0 (Ethanol) | $C_{20}H_{15}F_3N_2O_4S \cdot \frac{1}{4} H_2O$ | 54.47 / 54.60 | 3.55 / 3.42 | 6.35 / 6.37 |
| 21 | 3,5-$CF_3$ | 6-MeO | Double bond | 237.0~239.0 (DMF-ethanol) | $C_{21}H_{14}F_6N_2O_4S \cdot \frac{1}{2} H_2O$ | 49.12 / 49.04 | 2.95 / 3.01 | 5.46 / 5.43 |
| 22 | 4-t-Bu | 6-MeO | Single bond | 135.0~136.0 (Ethyl acetate-hexane) | $C_{23}H_{26}N_2O_4S$ | 64.77 / 64.97 | 6.14 / 6.31 | 6.57 / 6.32 |
| 23 | 4-t-Bu | 6-MeO | Double bond | 185.0~188.0 (Ethanol) | $C_{23}H_{24}N_2O_4S \cdot H_2O$ | 62.62 / 62.85 | 5.92 / 6.94 | 6.33 / 6.15 |
| 24 | 4-$CF_3O$ | 6-MeO | Double bond | 166.0~168.0 (Ethanol) | $C_{20}H_{15}F_3N_2O_5S$ | 53.09 / 52.83 | 3.34 / 3.68 | 6.19 / 5.88 |
| 25 | 4-MeO | 6-MeO | Double bond | 209.0~211.0 (DMF-ethanol) | $C_{20}H_{18}N_2O_5S$ | 60.29 / 60.35 | 4.55 / 4.55 | 7.03 / 7.03 |
| 26 | 3,4-MeO | 6-MeO | Single bond | Amorphous | $C_{21}H_{22}N_2O_6S \cdot \frac{1}{4} H_2O$ | 57.99 / 58.02 | 5.21 / 5.44 | 6.44 / 6.15 |

TABLE 6

| Example | R¹, R² | R³ | Dotted line portion | Melting point (° C.) (Recrystallization solvent) | Composition formula | Elemental analysis (%) Calculated/Found C | H | N |
|---|---|---|---|---|---|---|---|---|
| 27 | 3,4-methylenedioxy | 6-MeO | Double bond | 238.0~241.0 (DMF-ethanol) | $C_{20}H_{16}N_2O_6S$ | 58.24 / 58.17 | 3.91 / 3.98 | 6.79 / 6.80 |
| 28 | 4-F | 6-MeO | Single bond | Amorphous | $C_{19}H_{17}FN_2O_4S \cdot 1/2 H_2O$ | 57.41 / 57.12 | 4.56 / 4.61 | 7.05 / 7.24 |
| 29 | 4-$CF_3$ | 4-MeO | Single bond | 204.0~207.0 (Acetonitrile) | $C_{20}H_{17}F_3N_2O_4S$ | 54.79 / 54.76 | 3.91 / 3.92 | 6.39 / 6.55 |
| 30 | 3,4-methylenedioxy | 4-MeO | Single bond | 134.0~137.0 (Methylene chloride) | $C_{20}H_{18}N_2O_6S$ | 57.98 / 57.78 | 4.38 / 4.41 | 6.76 / 6.74 |
| 31 | H | 4-MeO | Single bond | 95.0~98.0 (Ethanol) | $C_{19}H_{18}N_2O_4S \cdot 3/5 H_2O$ | 59.85 / 59.79 | 5.09 / 5.18 | 7.35 / 7.37 |
| 32 | 4-$CF_3$ | 2-MeO | Single bond | 197.0~199.0 (Ethanol) | $C_{20}H_{17}F_3N_2O_4S$ | 54.79 / 54.70 | 3.91 / 3.84 | 6.39 / 6.39 |
| 33 | 4-$CF_3$ | 6-EtO | Double bond | 227.0~229.0 (DMF-ethanol) | $C_{21}H_{17}F_3N_2O_4S \cdot 1/2 H_2O$ | 54.90 / 54.83 | 3.95 / 3.82 | 6.10 / 5.98 |
| 34 | 3,4-methylenedioxy | 6-EtO | Double bond | 213.0~215.0 (DMF-ethanol) | $C_{21}H_{18}N_2O_6S$ | 59.14 / 58.99 | 4.25 / 4.32 | 6.57 / 6.70 |
| 35 | 4-$CF_3$ | 6-i-PrO | Double bond | 231.0~232.0 (Ethanol) | $C_{22}H_{19}F_3N_2O_4S$ | 56.89 / 56.68 | 4.12 / 4.11 | 6.03 / 6.02 |
| 36 | 4-$CF_3$ | 6-F | Single bond | 145.0~146.0 (Methylene chloride) | $C_{19}H_{14}F_4N_2O_3S$ | 53.52 / 53.36 | 3.31 / 3.22 | 6.57 / 6.62 |
| 37 | 4-$(Me)_2N$ | 6-MeO | Double bond | 203.0~208.0 (Washed with ethanol) | $C_{21}H_{21}N_3O_4S$ | * | | |
| 38 | 4-Me | 6-MeO | Double bond | 170.0~172.0 (Ethanol) | $C_{20}H_{18}N_2O_4S$ | MS (m/z) 382 (M⁺) | | |

*¹H NMR ($d_6$-DMSO), δ: 2.86(6H, s), 3.94(3H, s), 4.38(2H, d, J=5.9Hz), 6.69(2H, d, J=8.8Hz), 7.18(2H, d, J=8.8Hz), 7.28(1H, d, J=7.9Hz), 7.74(1H, dd, J=2, 2, 7.9Hz), 7.78(1H, s), 7.95(1H, d, J=2.2Hz), 8.59(1H, t, J=5.9Hz), 12.30(1H, br)

EXAMPLE 39

N-(4-Trifluoromethylbenzyl)-5-(2,4-dioxothiazolidin-5-yl)methyl-2-methoxybenzamide N-(4-Trifluoromethylbenzyl)-5-(2,4-dioxothiazolidin-5-ylidene)methyl-2-methoxybenzamide (500 mg) was suspended into ethanol (70 ml) and hydrogenated with 10% palladium/carbon (500 mg) at room temperature under a hydrogen pressure of 3.0 kg/cm². The reaction liquor was filtered and concentrated and the residue was purified by means of silica gel column chromatography (developing solvent; methylene chloride:methanol=50:1) to obtain 403 mg (80%) of aimed compound as crystals. Further, these were recrystallized from ethyl acetate to obtain purified aimed compound as colorless powdery crystals. Melting point 176.0~177.5° C.

Elemental analysis (%): For $C_{20}H_{17}F_3N_2O_4S$

|  | C | H | N |
|---|---|---|---|
| Calculated | 54.79 | 3.91 | 6.39 |
| Found | 54.75 | 3.84 | 6.40 |

EXAMPLES 40 THROUGH 48

Similarly to Example 39, compounds in Table 7 were obtained.

residue was purified by means of silica gel column chromatography (developing solvent; methylene chloride:methanol=40:1) to obtain 618 mg (80%) of aimed compound as crystals. These were recrystallized from ethanol-water to obtain purified aimed compound as a light brown powdery crystals. Melting point 146.0~148.0° C.

Elemental analysis (%): For $C_{19}H_{15}F_3N_2O_4S$

|  | C | H | N |
|---|---|---|---|
| Calculated | 53.77 | 3.56 | 6.60 |
| Found | 53.92 | 3.88 | 6.49 |

EXAMPLE 50

(−)-N-(4-Trifluoromethylbenzyl)-5-(2,4-dioxothiazolidin-5-yl)methyl-2-methoxybenzamide

TABLE 7

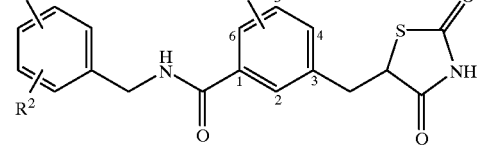

| Example | R¹ · R² | R³ | Melting point (°C.) (Recrystallization solvent) | Composition formula | Elemental analysis (%) Calculated/Found C | H | N |
|---|---|---|---|---|---|---|---|
| 40 | 3, 5-CF₃ | 6-MeO | 167.0~169.0 (Ethanol) | $C_{21}H_{16}F_6N_2O_4S$ | 49.80 / 50.00 | 3.19 / 3.06 | 5.53 / 5.54 |
| 41 | 4-Me | 6-MeO | Amorphous | $C_{20}H_{20}N_2O_4S$ | 62.48 / 62.20 | 5.24 / 5.23 | 7.29 / 7.30 |
| 42 | 4-CF₃O | 6-MeO | Amorphous | $C_{20}H_{17}F_3N_2O_5S$ | 52.86 / 52.68 | 3.77 / 3.80 | 6.17 / 6.45 |
| 43 | 4-MeO | 6-MeO | Amorphous | $C_{20}H_{20}N_2O_5S$ · ¼ $H_2O$ | 59.31 / 59.24 | 5.11 / 5.03 | 6.92 / 6.94 |
| 44 | 3, 4-methylenedioxy | 6-MeO | Amorphous | $C_{20}H_{18}N_2O_6S$ · ¼ $H_2O$ | 57.33 / 57.10 | 4.46 / 4.38 | 6.69 / 6.89 |
| 45 | 4-(Me)₂N | 6-MeO | Amorphous | $C_{21}H_{23}N_3O_4S$ · ¼ $H_2O$ | 60.33 / 60.48 | 5.68 / 5.66 | 10.05 / 10.13 |
| 46 | 4-CF₃ | 6-EtO | 159.0~162.0 (Ethanol) | $C_{21}H_{19}F_3N_2O_4S$ | 55.74 / 55.65 | 4.23 / 4.25 | 6.19 / 6.34 |
| 47 | 3, 4-methylenedioxy | 6-EtO | Amorphous | $C_{21}H_{20}N_2O_6S$ | 58.87 / 58.59 | 4.71 / 4.85 | 6.54 / 6.72 |
| 48 | 4-CF₃ | 6-i-PrO | 158.0~158.5 (Ethyl acetate-hexane) | $C_{22}H_{21}F_3N_2O_4S$ | 56.65 / 56.70 | 4.54 / 4.44 | 6.01 / 5.98 |

EXAMPLE 49

N-(4-Trifluoromethylbenzyl)-5-(2,4-dioxothiazolidin-5-yl)methyl-2-hydroxybenzamide To a suspension of N-(4-trifluoromethylbenzyl)-5-(2,4-dioxothiazolidin-5-yl)methyl-2-methoxybenzamide (800 mg) in anhydrous methylene chloride (30 ml), a 1.0N boron tribromidemethylene chloride solution (2.20 ml) was slowly added dropwise in an argon atmosphere under cooling with dry ice-acetone and stirring. After stirred for 6 hours at room temperature, the reaction liquor was allowed to stand for 3 days. After water was added and the mixture was stirred for 30 minutes, this was concentrated under reduced pressure. Ethyl acetate was added to the residue, which was washed with water and then dried over anhydrous sodium sulfate. This was concentrated under reduced pressure and the Into 20 ml of ethyl acetate, 1.00 g of (±)-N-(4-trifluoromethylbenzyl)-5-(2,4-dioxothiazolidin-5-yl)methyl-2-methoxybenzamide obtained in Example 39 was dissolved under heat. After cooling, 0.276 g of L(−)-phenethylamine were added and the mixture was allowed to stand for a week at room temperature. The crystals deposited were filtered, washed with ethyl acetate and dried to obtain 0.753 g of L(−)-phenethylamine salt as white flaky crystals. Further, these were recrystallized from ethyl acetate to obtain 0.142 g of second crystals and 0.0908 g of third crystals. Melting point 191~193° C., Optical rotation $[\alpha]_D = -87°$ (C=0.24, THF)

Elemental analysis (%): For $C_{28}H_{28}F_3N_3O_4S$

|  | C | H | N |
|---|---|---|---|
| Calculated | 60.10 | 5.04 | 7.51 |
| Found | 60.24 | 5.05 | 7.43 |

To 20 ml of 1N hydrochloric acid, 0.753 g of first crystals were added under ice cooling. The mixture was stirred for 5 minutes and then filtered, and the crystals were washed with water and dried by heating. The crystals thus obtained were recrystallized from ethanol to obtain 0.532 g of aimed product as white powdery crystals. Melting point 194~195° C., Optical rotation $[\alpha]_D = -100°$ (C=0.24, THF)

Elemental analysis (%): For $C_{20}H_{17}F_3N_2O_4S$

|  | C | H | N |
|---|---|---|---|
| Calculated | 54.79 | 3.91 | 6.39 |
| Found | 54.72 | 3.90 | 6.35 |

For measuring the optical purity, part of crystals obtained (ca. 1 mg) was sampled and dissolved into 3 ml of methanol. After cooling, 0.2 ml of diazomethane-ether solution were added and, after stirred for 5 minutes at room temperature, solvent was distilled off under reduced prssure. Further, after distilled off the residual solvent for one hour with pump for distillation under reduced pressure, the residue was dissolved into methanol, and the optical purity was measured by means of liquid chromatography (column; chiral cell AD (Daicel), eluting solvent; hexane:isopropanol=70:30, flow rate; 1.0 ml/min, measuring wavelength; λ=230 nm, retention time; 22.31 min) to obtain 99.2% ee.

EXAMPLE 51
(+)-N-(4-Trifluoromethylbenzyl)-5-(2,4-dioxothiazolidin-5-yl)methyl-2-methoxybenzamide Similarly to Example 50, 1.00 g of (±)-N-(4-trifluoromethylbenzyl)-5-(2,4-dioxothiazolidine-5-yl) methyl-2-methoxybenzamide obtained in Example 39 was submitted to the optical resolution with D(+)-phenethylamine to obtain 0.742 g of first crystals, 0.143 g of second crystals and 0.0587 g of third crystals as white flaky crystals for D(+)-phenethylamine salt. Melting point 191~193° C., Optical rotation $[\alpha]_D = 87°$ (C=0.24, THF)

Elemental analysis (%): For $C_{28}H_{28}F_3N_3O_4S$

|  | C | H | N |
|---|---|---|---|
| Calculated | 60.10 | 5.04 | 7.51 |
| Found | 59.95 | 5.19 | 7.49 |

Similarly to Example 50, 0.742 g of first crystals were treated with iN hydrochloric acid and recrystallized from ethanol to obtain 0.510 g of aimed product as white powdery crystals. Melting point 194~195° C., Optical rotation $[\alpha]_D = 100°$ (C=0.24, THF)

Elemental analysis (%): For $C_{20}H_{17}F_3N_2O_4S$

|  | C | H | N |
|---|---|---|---|
| Calculated | 54.79 | 3.91 | 6.39 |
| Found | 54.88 | 4.03 | 6.42 |

For measuring the optical purity, N-methylation was made with diazomethane similarly to Example 50, and then the optical purity was measured by means of liquid chromatography (column; chiral cell AD (Daicel), eluting solvent; hexane:isopropanol=70:30, flow rate; 1.0 ml/min, measuring wavelength; λ=230 nm, retention time; 30.64 min) to obtain 99.2% ee.

TEST EXAMPLE 1

Employing inherited obese mice (C57BL ob/ob), the value of blood sugar was determined by collecting blood from caudal vein prior to testing. They were grouped so as not to cause any difference in the values of blood sugar, and the compounds of Example 36, 39, 46 and 48 were administered orally for 5 days at a dosage of 10 mg/kg, respectively. For the glucose resistance test, 2 g/kg of glucose were administered orally after fasted overnight and the values of blood sugar at 0 minute, 30 minutes and 60 minutes were determined. The blood sugar-lowering rate was calculated from following formula.

Blood sugar-lowering rate (%) =

$$\frac{\begin{array}{l}[(\text{Sum of values of blood sugar of vehicle control group}\\ \text{at 0, 30 and 60 minutes after administration of glucose}) - \\ (\text{Sum of values of blood sugar of each group at 0, 30}\\ \text{and 60 minutes after administration of glucose})]\end{array}}{\begin{array}{l}(\text{Sum of values of blood sugar of vehicle control group}\\ \text{at 0, 30 and 60 minutes after administration of glucose})\end{array}} \times 100$$

Results are shown in Table 8. From these results, it was shown that the inventive compounds had potent hypoglycemic effects.

TABLE 8

| Compound | Dosage (mg/kg) | Blood sugar-lowering rate (%) |
|---|---|---|
| Example 36 | 10 | 43 |
| Example 39 | 10 | 47 |
| Example 46 | 10 | 37 |
| Example 48 | 10 | 45 |

TEST EXAMPLE 2

Employing inherited obese mice (C57BL ob/ob), value of triglyceride in blood and value of free fatty acid in blood were determined by collecting blood from caudal vein prior to testing and they were grouped. After the compound of Example 39 was administered orally for 2 weeks at following dosages, the value of triglyceride in blood and the value of free fatty acid in blood were determined. The lowering rate of each parameter was calculated from following formula.

Lowering rate (%) =

$$\frac{[(\text{Value measured for vehicle control group}) - \\ (\text{Value measured for each group of compound administration})]}{(\text{Value measured for vehicle control group})} \times 100$$

Results are shown in Table 9. From these results, it was shown that the inventive compound had potent lipid-lowering effects.

TABLE 9

| Compound | Dosage (mg/kg) | Lowering rate of triglyceride in blood (%) | Lowering rate of free fatty acid in blood (%) |
|---|---|---|---|
| Example 39 | 1 | 28 | 26 |
|  | 3 | 42 | 29 |

As above, with the N-benzyldioxothiazolidylbenzamide derivatives in accordance with the invention, drugs that improve the insulin resistance in the non-insulin dependent type diabetes mellitus and have potent hypoglycemic effects and high safety can be obtained.

We claim:

1. An N-Benzyldioxothiazolidylbenzamide derivative represented by a general formula (1)

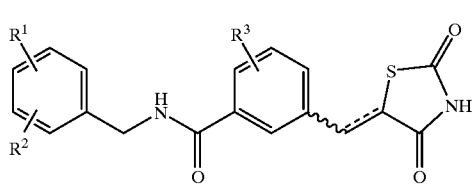

wherein $R^1$ and $R^2$ denote identically or differently hydrogen atoms, lower alkyl groups with carbon atoms of 1 to 4, lower alkoxy groups with carbon atoms of 1 to 3, lower haloalkyl groups with carbon atoms of 1 to 3, lower haloalkoxy groups with carbon atoms of 1 to 3, halogen atoms, hydroxyl groups, nitro groups, amino groups optionally substituted with lower alkyl group(s) with carbon atoms of 1 to 3 or hetero rings, or $R^1$ and $R^2$ link to form a methylenedioxy group, $R^3$ denotes a lower alkoxy group with carbon atoms of 1 to 3, hydroxyl group or halogen atom, and dotted line indicates double bond or single bond in combination with solid line, or a pharmacologically acceptable salt.

2. An N-Benzyldioxothiazolidylbenzamide derivative of claim 1, wherein the derivative is N-(4-trifluoromethylbenzyl)-5-(2,4-dioxothiazolidin-5-yl)methyl-2-methoxybenzamide, or a pharmacologically acceptable salt thereof.

3. An N-Benzyldioxothiazolidylbenzamide derivative of claim 1, wherein the derivative is N-(4-trifluoromethylbenzyl)-5-(2,4-dioxothiazolidin-5-yl)methyl-2-isopropoxybenzamide, or a pharmacologically acceptable salt thereof.

4. An N-Benzyldioxothiazolidylbenzamide derivative of claim 1, wherein the derivative is N-(4-trifluoromethylbenzyl)-5-(2,4-dioxothiazolidin-5-yl)methyl-2-ethoxybenzamide, or a pharmacologically acceptable salt thereof.

5. An N-Benzyldioxothiazolidylbenzamide derivative of claim 1, wherein the derivative is N-(4-trifluoromethylbenzyl)-5-(2,4-dioxothiazolidin-5-yl)methyl-2-fluorobenzamide, or a pharmacologically acceptable salt thereof.

6. A hypoglycemic agent comprising at least one N-benzyldioxothiazolidylbenzamide derivative represented by a general formula (1)

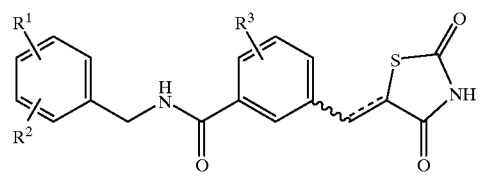

wherein $R^1$ and $R^2$ denote identically or differently hydrogen atoms, lower alkyl groups with carbon atoms of 1 to 4, lower alkoxy groups with carbon atoms of 1 to 3, lower haloalkyl groups with carbon atoms of 1 to 3, lower haloalkoxy groups with carbon atoms of 1 to 3, halogen atoms, hydroxyl groups, nitro groups, amino groups optionally substituted with lower alkyl group(s) with carbon atoms of 1 to 3 or hetero rings, or $R^1$ and $R^2$ link to form a methylenedioxy group, $R^3$ denotes a lower alkoxy group with carbon atoms of 1 to 3, hydroxyl group or halogen atom, and dotted line indicates double bond or single bond in combination with solid line, or a pharmacologically acceptable salt thereof as an effective component(s).

7. A hypoglycemic agent as in claim 6 wherein the derivative is N-(4-trifluoromethylbenzyl)-5-(2,4-dioxothiazolidin-5-yl)methyl-2-methoxybenzamide, or a pharmacologically acceptable salt thereof.

8. A hypoglycemic agent as in claim 6, wherein the derivative is N-(4-trifluoromethylbenzyl)-5-(2,4-dioxothiazolidin-5-yl)methyl-2-isopropoxybenzamide, or a pharmacologically acceptable salt thereof.

9. A hypoglycemic agent as in claim 6, wherein the derivative is N-(4-trifluoromethylbenzyl)-5-(2,4-dioxothiazolidin-5-yl)methyl-2-ethoxybenzamide, or a pharmacologically acceptable salt thereof.

10. A hypoglycemic agent as in claim 6, wherein the derivative is N-(4-trifluoromethylbenzyl)-5-(2,4-dioxothiazolidin-5-yl)methyl-2-fluorobenzamide, or a pharmacologically acceptable salt thereof.

11. A process for preparing an N-benzyldioxothiazolidylbenzamide derivative represented by a general formula (1)

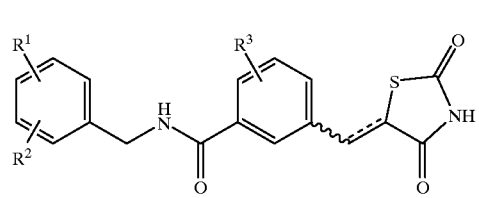

wherein $R^1$ and $R^2$ denote identically or differently hydrogen atoms, lower alkyl groups with carbon atoms of 1 to 4, lower alkoxy groups with carbon atoms of 1 to 3, lower haloalkyl groups with carbon atoms of 1 to 3, lower haloalkoxy groups with carbon atoms of 1 to 3, halogen atoms, hydroxyl groups, nitro groups, amino groups optionally substituted with lower alkyl group(s) with carbon atoms of 1 to 3 or hetero rings, or $R^1$ and $R^2$ link to form a methylenedioxy group, $R^3$ denotes a lower alkoxy group with carbon atoms of 1 to 3, hydroxyl group or halogen atom, and dotted line indicates double bond or single bond in combination with solid line, characterized by reacting a compound represented by general formula (7)

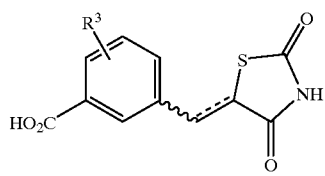
(7)

wherein R³ and dotted line are as described above, with a compound represented by general formula (11)

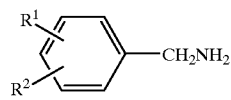
(II)

wherein R¹ and R² are as described above.

12. A process for preparing an N-benzyldioxothiazolidylbenzamide derivative represented by a general formula (1b)

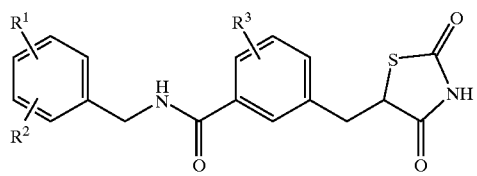
(Ib)

wherein R¹ and R² denote identically or differently hydrogen atoms, lower alkyl groups with carbon atoms of 1 to 4, lower alkoxy groups with carbon atoms of 1 to 3, lower haloalkyl groups with carbon atoms of 1 to 3, lower haloalkoxy groups with carbon atoms of 1 to 3, halogen atoms, hydroxyl groups, nitro groups, amino groups optionally substituted with lower alkyl group(s) with carbon atoms of 1 to 3 or hetero rings, or R¹ and R² link to form a methylenedioxy group, and R³ denotes a lower alkoxy group with carbon atoms of 1 to 3, hydroxyl group or halogen atom, characterized by reducing a compound represented by general formula (1a)

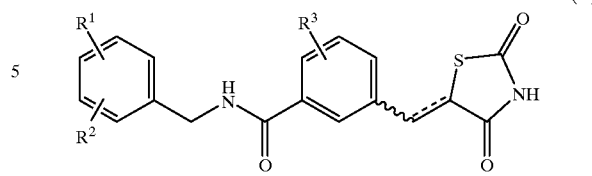
(Ia)

wherein R¹, R² and R³ are as described above.

13. A process for preparing an N-benzyldioxothiazolidylbenzamide derivative represented by a general formula (1d)

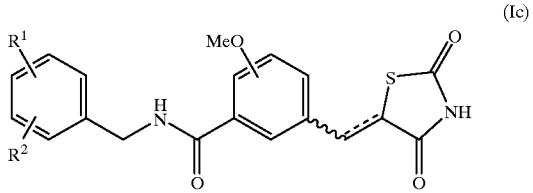
(Id)

wherein R¹ and R² denote identically or differently hydrogen atoms, lower alkyl groups with carbon atoms of 1 to 4, lower alkoxy groups with carbon atoms of 1 to 3, lower haloalkyl groups with carbon atoms of 1 to 3, lower haloalkoxy groups with carbon atoms of 1 to 3, halogen atoms, hydroxyl groups, nitro groups, amino groups optionally substituted with lower alkyl group(s) with carbon atoms of 1 to 3 or hetero rings, or R¹ and R² link to form a methylenedioxy group, and dotted line indicates double bond or single bond in combination with solid line, characterized by reducing a compound represented by general formula (1c)

(Ic)

wherein R¹, R² and dotted line are as described above, with Lewis acid.

* * * * *